United States Patent
Jiao et al.

(10) Patent No.: US 8,927,008 B2
(45) Date of Patent: *Jan. 6, 2015

(54) COMPOUND SEA CUCUMBER PRODUCT, PREPARATION METHOD, AND DOSAGE FORMS THEREOF

(75) Inventors: Jian Jiao, Dalian (CN); Junjie Shao, Dalian (CN)

(73) Assignee: Dalian Haiyantang Biology Co., Ltd., Dalian, Liaoning (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/576,972

(22) PCT Filed: Mar. 3, 2011

(86) PCT No.: PCT/CN2011/071482
§ 371 (c)(1),
(2), (4) Date: Aug. 3, 2012

(87) PCT Pub. No.: WO2012/079311
PCT Pub. Date: Jun. 21, 2012

(65) Prior Publication Data
US 2012/0321704 A1      Dec. 20, 2012

(30) Foreign Application Priority Data
Dec. 14, 2010   (CN) .......................... 2010 1 0586826

(51) Int. Cl.
*A61K 9/48*  (2006.01)
*A61K 36/258*  (2006.01)
*A23L 1/327*  (2006.01)
*A61K 35/56*  (2006.01)

(52) U.S. Cl.
CPC .............. *A61K 36/258* (2013.01); *A23L 1/327* (2013.01); *A61K 35/616* (2013.01); *A23V 2002/00* (2013.01); *A61K 2236/39* (2013.01)
USPC ....................................................... 424/451

(58) Field of Classification Search
None
See application file for complete search history.

(56) References Cited

FOREIGN PATENT DOCUMENTS

| | | | |
|---|---|---|---|
| CN | 100998427 | * | 7/2007 |
| CN | 101143155 | | 3/2008 |
| CN | 100432232 | | 11/2008 |
| CN | 101416672 | * | 4/2009 |
| CN | 101416757 | | 4/2009 |
| CN | 101700265 | * | 11/2009 |
| WO | 2007005349 | | 1/2007 |

* cited by examiner

Primary Examiner — Snigdha Maewall
(74) Attorney, Agent, or Firm — Novick, Kim & Lee, PLLC; Allen Xue

(57) ABSTRACT

A compound sea cucumber product, preparation method thereof and dosage forms thereof are disclosed. A fresh sea cucumber is cut open, the viscus thereof is taken out, and they are well-cleaned respectively and put into an airtight container; at 70~130° C., gelatinate for 1 min~20 hours; thereafter freeze-dry till the water content is less than 10 wt %; apply coarse crushing till the fineness reaches 10~300 mesh; then apply ultra-micro crushing by means of an airflow crusher until the fineness reaches 100~3000 mesh; lastly apply nanometer crushing by means of high-energy ball grinding mill till the fineness reaches 10~1000 nm. The nanometer sea cucumber extract is mixed with panax pseudo-ginseng saponins extract at the proportion of 99~80 wt %:1~20 wt %. The compound preparation of nanometer sea cucumber and panax pseudo-ginseng saponins can greatly enhance the pharmacological functions of the sea cucumber single preparation or the panax pseudo-ginseng single preparation and eliminate the side effects of the single preparations when used alone. The compound preparation can achieve a better health-care effect than the single preparations and it can be applied for various health-care and medicinal purposes.

12 Claims, No Drawings

COMPOUND SEA CUCUMBER PRODUCT, PREPARATION METHOD, AND DOSAGE FORMS THEREOF

TECHNICAL FIELD

The invention relates to medicinal preparation of extract from mollusca and plant.

BACKGROUND TECHNOLOGY

Sea cucumber is one of the eight sea food treasures in China, and its nourishing values are known to all. Wherein the sea cucumber polysaccharide is the most important active ingredient of sea cucumber and has a variety of physiological activities, according to the experiment and research, sea cucumber polysaccharides has remarkable effect against cardiovascular diseases. To develop directly after nanorizing the sea cucumber not only can sufficiently use the active ingredients such as sea cucumber polysaccharide, meanwhile, also can commonly sufficiently use the sea cucumber protein, lipid and so on.

Pseudo-ginseng is a specialty in southern Yunnan Province and is a panax plant, the meat quality of rootstock is like ginger shape, using for curing traumatic injuries, blood activation and stasis remove etc in folk. The main functional component of pseudo-ginseng is panax Pseudo-ginseng saponins widely used in medicinal healthcare field, and pharmaceutical enterprises develop many famous medicines such as Yunnan Baiyao, Blood-block Unlock series, Compound *Salvia Miltiorrhiza* Dripping Pills, Pien Tze Huang by using the special effect of pseudo-ginseng. Wherein, medicines made from panax Pseudo-ginseng saponins are generally called "Thrombus Unlock", at present blood-block unlock injections, blood-block unlock pills, blood-block capsules and blood-block unlock granules etc can be fund in the market. Blood-block unlock is a mandatory drug kept in storage by the emergency departments of all Chinese hospitals, and is mainly used in relation to heart cerebrovascular diseases.

Modern science and technology development has confirmed the effect of the active ingredients in sea cucumber and pseudo-ginseng to human body, and numerous medicines and health care products are produced and appear in the market. However the important research subject at present is that whether compound preparation of each characteristic of sea cucumber and pseudo-ginseng etc has a better effect to human body health or not.

Sea cucumber compound preparation is mainly empty in the market at present, only a few such as Patent 200710114414.7 Compound Sea Cucumber Glycopeptide Oral Liquid, which is a compound sea cucumber oral liquid developed by using sea cucumber, matched with royal jelly and Chinese medicine extract, and the aiming crowd is unclear and the effect is unclear.

SUMMARY OF THE INVENTION

The purpose of the invention is to develop a product which has a better treatment and health care effect than only using sea cucumber or pseudo-ginseng through using the polysaccharide extracted from the atomized sea cucumber nanometer powder and directly matching with pseudo-ginseng or panax pseudo-ginseng saponins extract.

The technical proposal of the invention is to firstly gelatinate the sea cucumber, the gelatinated sea cucumber is crushed into nanometer particles sequentially by coarse crushing, ultra-micro crushing and nanometer crushing after freeze-drying, then prepare the extract by enzymolysis and separating the nanometer sea cucumber particles (active ingredient: sea cucumber polysaccharide), at last compound prepare the product with the sea cucumber extract and panax pseudo-ginseng saponins.

The detail operation steps of the proposal comprising:

(1) Raw material process: put the cut and well-cleaned fresh sea cucumber or soaked sea cucumber into an airtight container; cut the fresh sea cucumber and take out the viscus, wash them respectively and sufficiently, may use only sea cucumber body, also may grind with the sea cucumber viscus and put into an airtight container. The varieties of said fresh sea cucumber or soaked sea cucumber are common eatable sea cucumber such as sea *stichopus* or *cucumaria frondosa*; said soaked sea cucumber is made by soaking or desalinating dry sea cucumber, half-dried sea cucumber or saline sea cucumber.

(2) Heat and gelatination: heat at 70~130° C. for 1 min~20 h, preferably 100~105° C., 1 hour.

(3) Freeze-dry: freeze-dry the gelatinated sea cucumber till the water content is less than 10 wt %. In order to be good for subsequent crushing process, a lower water content after drying is preferred, preferably water content less than 3%.

(4) Coarse crush: crush the freeze-dried sea cucumber. A higher power of equipment for coarse crushing is preferred, the crush time is short and generally sea cucumber powder with fineness of 10~300 mesh can be made within 1~20 min.

(5) Ultra-micro crush: ultra-micro crush the coarse crushed sea cucumber powder with an airflow crusher, to get the ultra-micro sea cucumber powder with fineness of 100~3000 mesh;

(6) Nanometer crush: nanometer crush the ultra-micro sea cucumber powder by the airflow crusher with a high energy ball grinding mill, the crush time is 4~20 h, preferably 10~12 h, the fineness can be up to 10~1000 nm. Wherein X-ray is used to detect the particle size distribution, in 0~300 nm range, the average particle diameter is 100~200 nm.

(7) Mix the nanometer sea cucumber extract with the panax pseudo-ginseng saponins extract at the ratio of nanometer sea cucumber extract:panax pseudo-ginseng saponins extract equal to 99~70 wt %:1~30 wt %.

(8) Various dosage forms, such as capsules, pills and granules can be made after mixing.

This product is a gray or light brown or brown powder and the main active ingredient is sea cucumber polysaccharide and panax pseudo-ginseng saponins (calculated by R1+Rb1+Rg1 ingredient total contents), the content of sea cucumber polysaccharide is 2.5%~8.0% and the content of panax pseudo-ginseng saponins is 0.3%~21%.

The efficacy experiment of the invention proves that: the high and low dosage groups of compound sea cucumber products have obvious inhibition for the vein thrombosis of rats, the inhibition rates respectively are 88.9% and 81.5%; the compound sea cucumber products can decrease the blood specific viscosity of rats at high and low shear rates, but have no significant influence on blood plasma specific viscosity, showing that the effect of sea cucumber to decrease the blood viscosity is from the influence to red blood cell, it can decrease the aggregation of red blood cell and also can enhance the deformability, and the improving effect of sea cucumber powder to blood rheology becomes one of the main pharmacological basis of its anti-thrombotic effect.

The experiment of blood platelet aggregation internal and external comparing the compound sea cucumber product with pure nanometer sea cucumber powder shows that: pure nanometer sea cucumber powder has the effect of platelet aggregation promotion; however the effect of platelet aggregation promotion of compound sea cucumber product is not significant. The experiment of the invention also proves that: the comparison of anticoagulant activity and anti-thrombotic activity of different varieties of sea cucumbers has no significant differences.

The invention uses the atomized sea cucumber nanometer powder directly matched with pseudo-ginseng (saponins extract) to develop a health care food which mainly has significant effect on heart cerebrovascular diseases. The present research shows that sea cucumber polysaccharide not only has anti-coagulation function, also can mobilize the capability of stem cell from the bone marrow, while panax pseudo-ginseng saponins can promote the mobilized hepatic stem cells to transform or differentiate into new myocardial cells or brain cells, so as to replace the myocardium or brain necrosis caused by ischemia. The compound preparation of nanometer sea cucumber and panax pseudo-ginseng saponins have complementary and collaboration effect in pharmacological effects, the side effect that sea cucumber polysaccharide can promote the blood platelet aggregation can be eliminated through the compound preparation with panax pseudo-ginseng saponins. The compound preparation of nanometer sea cucumber and panax pseudo-ginseng saponins can greatly enhance the pharmacological functions of single formular of sea cucumber or pseudo-ginseng, and can be widely used in various medicinal purposes.

Hence, compared with present technologies, an outstanding characteristic of the invention is to compound prepare the nanometer sea cucumber and panax pseudo-ginseng saponins in a good way, eliminate the disadvantages caused by the conventional single use methods, so as to obtain a better health-care effect than the conventional technologies using the single use methods.

DETAILED DESCRIPTION OF EMBODIMENTS

I. Manufacture of Compound Sea Cucumber Preparation

Example 1

(1) Raw material processing: cut the fresh sea *stichopus*, take out the viscus, sufficiently clean the sea cucumber wall, put into an airtight container;

(2) Heat and gelatination: at 70~80° C., heat for 20 hours;

(3) Vacuum Freeze-dry: freeze-dry the gelatinated sea cucumber till the water content is less than 0.1 wt %;

(4) Coarse crush: crush the freeze-dried sea cucumber to obtain sea cucumber powder with fineness of 10~300 mesh;

(5) Ultra-micro crush: ultra-micro crush the coarse crushed sea cucumber powder with an airflow crusher, to obtain the ultra-micro sea cucumber powder with fineness of 100~3000 mesh;

(6) Nanometer crush: nanometer crush, by means of a high energy ball grinding mill, the ultra-micro sea cucumber powder obtained by the airflow crusher, for 4 hours;

(7) Mix the nanometer sea cucumber powder with panax pseudo-ginseng saponins extract at a mass ratio of nanometer sea cucumber powder:panax pseudo-ginseng saponins extract equal to 99%:1%. The panax pseudo-ginseng saponins extract may be manufactured by Nanjing ZeLang Medical Technology Co. Ltd.

The product is a gray powder, its main active ingredients are sea cucumber polysaccharide at 7.28 wt % and panax pseudo-ginseng saponins (calculated by R1+Rb1+Rg1 ingredient total contents) at 0.3 wt %. After mixing, the powder is made into capsules. Each capsule weighs 0.3 g.

Experiment is carried out for the compound sea cucumber product according to the above formula with respect to its influence on thrombus and blood rheology, and the results regarding the blood coagulation and anti-thrombotic effect of the sea cucumber compound product on animals are shown as below.

Example 2

(1) Raw material processing: cut the fresh *cucumaria frondosa*, take out the viscus, sufficiently clean the *cucumaria frondosa* wall and the viscus respectively, and put them together into an airtight container;

(2) Heat and gelatination: at 90~95° C., heat for 6 hours;

(3) Vacuum Freeze-dry: freeze-dry the gelatinated sea cucumber till the water content is less than 3 wt %;

(4) Coarse crush: crush the freeze-dried sea cucumber to obtain sea cucumber powder with fineness of 10~300 mesh;

(5) Ultra-micro crush: ultra-micro crush the coarse crushed sea cucumber powder with an airflow crusher, to obtain the ultra-micro sea cucumber powder with fineness of 100~3000 mesh;

(6) Nanometer crush: nanometer crush, by means of a high energy ball grinding mill, the ultra-micro sea cucumber powder obtained by the airflow crusher, for 10 hours;

(7) Mix the nanometer sea cucumber powder with panax pseudo-ginseng saponins extract at a mass ratio of nanometer sea cucumber powder:panax pseudo-ginseng saponins extract equal to 80% wt:20 wt %.

The product is a gray powder, its main active ingredients are sea cucumber polysaccharide at 3.8% and panax pseudo-ginseng saponins (calculated by R1+Rb1+Rg1 ingredient total contents) at 12.5%.

(8) After mixing, the powder is made into capsules. Each capsule weighs 0.3 g.

Experiment is carried out for the product with respect to blood platelet aggregation of external and internal of animals, and the results of the effect of the sea cucumber compound product on blood coagulation and anti-thrombotic with respect to animals are shown below.

Example 3

(1) Raw material processing: cut the fresh *cucumaria frondosa*, take out the viscus, sufficiently clean the *cucumaria frondosa* wall and the viscus respectively, and put them together into an airtight container;

(2) Heat and gelatination: at 100~105° C., heat for 4 hours;

(3) Vacuum Freeze-dry: freeze-dry the gelatinated sea cucumber till the water content is less than 3 wt %;

(4) Coarse crush: crush the freeze-dried sea cucumber to obtain sea cucumber powder with fineness of 10~300 mesh;

(5) Ultra-micro crush: ultra-micro crush the coarse crushed sea cucumber powder with an airflow crusher, to obtain the ultra-micro sea cucumber powder with fineness of 100~3000 mesh;

(6) Nanometer crush: nanometer crush, by means of a high energy ball grinding mill, the ultra-micro sea cucumber powder obtained by the airflow crusher, for 12 hours;

(7) Mix the nanometer sea cucumber powder with panax pseudo-ginseng saponins extract at a mass ratio of nanometer sea cucumber powder:panax pseudo-ginseng saponins extract equal to 90 wt %:10 wt %.

(8) After mixing, the powder is made into capsules. Each capsule weighs 0.3 g.

The product is a light yellow powder, its main active ingredients are sea cucumber polysaccharide at 4.7% and panax pseudo-ginseng saponins (calculated by R1+Rb1+Rg1 ingredient total contents) at 6.3%.

Example 4

(1) Raw material processing: cut the saline dry sea *stichopus*, soak it in water until it is softened, cut the sea *stichopus* wall, sufficiently clean, and put it into an airtight container.

(2) Gelatination: heat the container at 100~105° C. for 0.8 hours.

(3) Vacuum freeze-dry: freeze-dry the gelatinated sea cucumber till the water content is 5 wt %.

(4) Coarse crush: crush the freeze-dried sea cucumber to obtain sea cucumber powder with fineness of 10~300 mesh;

(5) Ultra-micro crush: ultra-micro crush the coarse crushed sea cucumber powder with an airflow crusher, to obtain the ultra-micro sea cucumber powder with fineness of 100~3000 mesh;

(6) Nanometer crush: nanometer crush, by means of a high energy ball grinding mill, the ultra-micro sea cucumber powder obtained by the airflow crusher, for 16 hours;

(7) Mix the nanometer sea cucumber extract with the panax pseudo-ginseng saponins extract at the ratio of nanometer sea cucumber extract:panax pseudo-ginseng saponins extract equal to 95 wt %:5 wt %.

The product is a light yellow powder, and the main active ingredients are sea cucumber polysaccharide and panax pseudo-ginseng saponins (calculated by R1+Rb1+Rg1 ingredient total contents), wherein the content of sea cucumber polysaccharide is 5.1 wt % and the content of panax pseudo-ginseng saponins is 2.3 wt %.

(8) After mixing make tablet at the ratio of raw material: excipients equal to 2:1. Each tablet weights 0.2 g.

Example 5

(1) Raw material processing: soak the dry *cucumaria frondosa*, when it is softened cut the *cucumaria frondosa* wall, after sufficiently cleaning, soak it, put into an airtight container.

(2) Gelatination: heat the container at 110~120° C. for 0.6 hours.

(3) Vacuum freeze-dry: freeze-dry the gelatinated sea cucumber till the water content is 7 wt %.

(4) Coarse crush: crush the freeze-dried sea cucumber to obtain sea cucumber powder with fineness of 10~300 mesh;

(5) Ultra-micro crush: ultra-micro crush the coarse crushed sea cucumber powder with an airflow crusher, to obtain the ultra-micro sea cucumber powder with fineness of 100~3000 mesh;

(6) Nanometer crush: nanometer crush, by means of a high energy ball grinding mill, the ultra-micro sea cucumber powder obtained by the airflow crusher, for 18 hours;

(7) Mix the nanometer sea cucumber extract with the panax pseudo-ginseng saponins extract at the ratio of nanometer sea cucumber extract:panax pseudo-ginseng saponins extract equal to 85 wt %:15 wt %.

The product is a light yellow powder, and the main active ingredients are sea cucumber polysaccharide and panax pseudo-ginseng saponins (calculated by R1+Rb1+Rg1 ingredient total contents), wherein the content of sea cucumber polysaccharide is 2.56 wt % and the content of panax pseudo-ginseng saponins is 3.9 wt %.

(8) After mixing make granules at the ratio of raw material: excipients equal to 1:1.

Example 6

(1) Raw material processing: cut the soaked sea *stichopus*, put into an airtight container.

(2) Gelatination: heat the container at 120~130° C. for 0.2 hours.

(3) Vacuum freeze-dry: freeze-dry the gelatinated sea cucumber till the water content is 9 wt %.

(4) Coarse crush: crush the freeze-dried sea cucumber to obtain sea cucumber powder with fineness of 10~300 mesh;

(5) Ultra-micro crush: ultra-micro crush the coarse crushed sea cucumber powder with an airflow crusher, to obtain the ultra-micro sea cucumber powder with fineness of 100~3000 mesh;

(6) Nanometer crush: nanometer crush, by means of a high energy ball grinding mill, the ultra-micro sea cucumber powder obtained by the airflow crusher, for 20 hours;

(7) Mix the nanometer sea cucumber extract with the panax pseudo-ginseng saponins extract at the ratio of nanometer sea cucumber extract:panax pseudo-ginseng saponins extract equal to 97 wt %:3 wt %.

The product is a light yellow powder, and the main active ingredients are sea cucumber polysaccharide and panax pseudo-ginseng saponins (calculated by R1+Rb1+Rg1 ingredient total contents), wherein the content of sea cucumber polysaccharide is 3.9 wt % and the content of panax pseudo-ginseng saponins is 1.19 wt %.

After mixing make granules at the ratio of raw material: excipients equal to 1:1.

II. Effects of Compound Sea Cucumber Products to Blood Coagulation and Anti-Thrombosis of Animals 1. Influences of Compound Sea Cucumber Products to Venous Thrombosis of Inferior Vena Cava of Rats 30 male SD rats with weight 180~220 g are divided into 3 groups randomly, those are normal saline (NS) group, compound sea cucumber products high dosage group, compound sea cucumber products low dosage group. Narcotize with urethane 1 $g \cdot kg^{-1}$, according to Rayers method, cut the abdominal wall in the middle, separate the inferior vena cava, and pre-set silk thread under the left kidney vein for ligation. NS group, compound sea cucumber capsules high and low dosage groups are respectively treated by irrigating stomachs with NS and drug for two weeks, and ligate inferior vena cava and close the abdomen 1 h after the last treating. Re-open the abdomen 4 h after ligation, and clip the vessels at 2 cm part under the ligation thread, meanwhile clip the main vein branches and draw residual blood absolutely with an injector, split the vessel longitudinally to observe whether thrombus is formed or not, if thrombus is formed, then toast the thrombus in a toaster at 60° C. for 20 min and weigh its dry weight, record the thrombosis animal numbers and thrombus dry weight. Calculate thrombosis ratio (thrombosis animal number/tested animal number) and thrombus dry weight inhibition percentage.

Compound sea cucumber products high and low dosage groups all have obvious inhibition effect to vein thrombosis of rats, the inhibition rates respectively are 88.9% and 81.5%. Results see Table 1:

TABLE 1

Results of compound sea cucumber products resistance to vein thrombosis of rats (n = 10)

| Group | Dosage (mg/Kg) | Thrombosis rate (thrombosis animal number/tested animal number) | Thrombus dry weight (mg) | Inhibition percentage (%) |
|---|---|---|---|---|
| NS | — | 10/10 | 2.7 ± 0.4 | — |
| Compound sea cucumber products | 900 | 8/10 | 0.3 ± 0.3*** | 88.9 |
| Compound sea cucumber products | 100 | 8/10 | 0.5 ± 0.3*** | 81.5 |

***P < 0.001 compared with normal saline groups

2. Influences of Compound Sea Cucumber Products to Blood Rheology 30 male SD rats with weight 180~220 g are divided into 3 groups randomly, those are normal saline (NS) group, compound sea cucumber products high dosage group, compound sea cucumber products low dosage group. Except NS group is treated by irrigating stomachs with equal volume NS, other dosage groups are treated for 2 weeks by irrigating stomachs, 1 h after the last time treating, narcotize animals with diethyl ether, collect blood 4.9 ml at abdominal aorta, put into a silicified test tube added with 0.1 ml 1.25% heparin, immediately determine blood rheology indexes at high shear rate and low shear rate with a blood rheometer such as blood specific viscosity, blood plasma specific viscosity etc.

The research shows that compound sea cucumber products can reduce the whole blood specific viscosity at high shear rate and low shear rate, but have no significant influence to blood plasma specific viscosity, showing that the effect of reducing blood viscosity by sea cucumber powder mainly comes from influences to red blood cells, which can reduce the aggregation of red blood cells, and also can enhance the deformability of blood red cells; the improving effects of sea cucumber powder to blood rheology become one of the main pharmacological basis of its anti-thrombosis effect. Results see Table 2.

TABLE 2

Influences of compound sea cucumber products to blood rheology of rats (n = 10)

| Group | Dosage (mg/Kg) | Whole blood specific viscosity $20S^{-1}$ | Whole blood specific viscosity $80S^{-1}$ | Blood plasma specific viscosity |
|---|---|---|---|---|
| NS | — | 33.27 ± 3.29 | 13.74 ± 1.31 | 2.127 ± 0.185 |
| Compound sea cucumber products | 900 | 9.99 ± 0.14* | 5.62 ± 0.27* | 2.082 ± 0.204 |
| Compound sea cucumber products | 100 | 10.51 ± 0.19* | 6.00 ± 0.23* | 2.133 ± 0.142 |

*P < 0.05, compared with normal saline

3. Experiment of Internal Blood Platelet Aggregation Comparing Compound Sea Cucumber Products with Pure Nanometer Sea Cucumber Powder:

(1) Experiment Design:

Grouping and treating for rats are the same as above said. Except NS group is treated by irrigating stomachs with equal volume NS, other treating groups are treated by irrigating stomachs for 2 weeks, collect blood on back abdomen aorta 1 h after the last time treating, respectively add 3.8% sodium citrate anti-coagulation (volume ratio between blood and anti-coagulation agent equal to 9:1), centrifuge for 10 min at 200×g to prepare platelet-rich plasma (PRP), centrifuge the residual blood for 10 min at 1200×g to prepare platelet-poor plasma (PPP). Adjust the platelet number in PRP to $4\text{-}5\times10^{12}$ $ml^{-1}$ with PPP, respectively take PRP 200 uL, add inducer ADP (ultimate concentration 2 $umol\cdot L^{-1}$), determine the platelet aggregation rate according to the turbidimetry proposed by Bron, and calculate the platelet aggregation promotion rate (%) according to formula below. Platelet aggregation determination is finished with 3 h.

Platelet Aggregation Promotion Rate=Treating Vessel Platelet Aggregation %−Control Vessel Platelet Aggregation %/Control Platelet Aggregation %×100%

Prepare high and low concentration M powder and N powder suspension respectively according to 200 mg:1 mL and 100 mg:1 mL, mix by volution for 1 min, extract the water soluble active ingredients, then centrifuge for 10 min at 3500 rpm, take the supernatant, that is aqueous extract for reservation.

Collect blood on the heart of domestic rabbit, add 3.8% sodium citrate anti-coagulation (volume ratio between blood and anti-coagulation agent equal to 9:1), prepare platelet-poor plasma (PPP) and platelet-rich plasma (PRP) according to the method in internal platelet aggregation experiment, take PRP 200 uL, add above prepared sea cucumber M powder and N powder aqueous extract 10 uL, then add inducer ADP (ultimate concentration 2 $umol\cdot L^{-1}$), determine the platelet aggregation rate according to Bron method.

(2) Experiment Results:

(i) Results of External Platelet Aggregation Experiment

Nanometer sea cucumber powder 200 mg:1 mL, 100 mg:1 mL both have the effect to promote the platelet aggregation externally, the aggregation promotion percentages are respectively 23.6% and 11.2%; compound sea cucumber products 200 mg:1 mL, 100 mg:1 mL aqueous extract have no significant platelet aggregation reaction externally, results see Table 3:

TABLE 3

Results of external platelet aggregation experiment of nanometer sea cucumber powder and compound sea cucumber products aqueous extracts (n = 10)

| Group | Aqueous extract concentration | Platelet aggregation rate (%) | Aggregation-promotion percentage (%) |
|---|---|---|---|
| NS | — | 67.77 ± 1.29 | — |
| Nanometer sea cucumber powder | 200 mg:1 mL | 83.79 ± 2.30* | 23.6 |
| Nanometer sea cucumber powder | 100 mg:1 mL | 75.37 ± 0.78*Δ | 11.2 |
| Compound sea cucumber products | 200 mg:1 mL | 73.29 ± 0.39*Δ | 8.1 |
| Compound sea cucumber products | 100 mg:1 mL | 68.57 ± 0.56* | 1.2 |

*P < 0.05, compared with normal saline group
ΔP < 0.05, compared with nanometer sea cucumber powder 200 mg:1 mL group (ii) Results of Internal Platelet Aggregation Experiment:

After treated by irrigating stomachs for 2 weeks with nanometer sea cucumber powder and compound sea cucumber product powder, nanometer sea cucumber powder has effect of platelet aggregation promotion. The platelet aggregation promotion ratios of the high and low dosage groups are respectively 47.1% and 24.3%. But the aggregation reaction of compound sea cucumber products is not significant, results see Table 4:

TABLE 4

Results of internal platelet aggregation experiment of nanometer sea cucumber powder and compound sea cucumber products (n = 10)

| Group | Dosage (mg/Kg) | Platelet aggregation rate (%) | Promotion percentage (%) |
| --- | --- | --- | --- |
| NS | — | 50.84 ± 1.57 | — |
| Nanometer sea cucumber powder | 900 | 74.79 ± 0.56* | 47.1 |
| Nanometer sea cucumber powder | 100 | 63.19 ± 1.80*$^\Delta$ | 24.3 |
| Compound sea cucumber products | 900 | 58.48 ± 1.11*$^\Delta$ | 15.0 |
| Compound sea cucumber products | 100 | 52.74 ± 1.68* | 3.7 |

*$P < 0.05$, compared with normal saline
$^\Delta P < 0.05$, compared with nanometer sea cucumber powder mg/Kg 4. Comparison of Anti-Coagulation Activity and Anti-Thrombus Activity Among Sea Cucumbers in Different Varieties (1) Comparison of anti-coagulation activity: 50 male Kunming mice are divided into 5 groups randomly: NS blank control group, 0.5 g/kg nanometer sea *stichopus* powder group, 0.5 g/kg nanometer *cucumaria frondosa* powder group. Mice are treated by irrigating stomachs with different sea cucumbers 0.5 g/kg twice each day, NS blank control group is treated with equal volume NS, after treating for 3 days continuously, determine the thrombin time (TT) and recalcification time (RT) with biological determination method, so as to compare the anti-coagulation activities between nanometer sea *stichopus* and nanometer *cucumaria frondosa* powder. Results see Table 5 below:

TABLE 5

Influences to TT and RT 3 days after mice are treated by irrigating stomachs with different sea cucumber powders (n = 10, x ± s)

| Group | Dosage | TT (s) | TT extension % | RT (s) | RT extension % |
| --- | --- | --- | --- | --- | --- |
| NS | | 5.80 ± 0.61 | — | 10.66 ± 3.08 | — |
| Nanometer sea stichopus powder | 0.5 g/kg | 7.56 ± 0.43*** | 30.34 | 60.84 ± 9.98*** | 470.73 |
| Nanometer cucumaria frondosa powder | 0.5 g/kg | 7.69 ± 0.62*** | 32.59 | 65.87 ± 9.00*** | 517.92 |

Note:
***$P < 0.001$ compared with NS group

As can be seen from Table 5, the thrombin times (TT) ($p<0.001$) and re-calcification time (RT) ($p<0.001$) are all significantly extended by treating by irrigating stomachs of mice with 0.5 g/kg above said two different nanometer sea cucumber powders, showing that above said two nanometer sea cucumber powder have significant anti-coagulation activities.

(2) Comparison of anti-thrombus activity: 60 male Kunming mice are divided into 6 groups: blank control group, thrombus model group, 0.5 g/kg nanometer *cucumaria frondosa* powder group, and 0.5 g/kg nanometer sea *stichopus* powder group. Mice are treated by irrigating stomachs with different sea cucumbers 0.5 g/kg twice each day, NS blank control group and thrombus model group are treated by irrigating stomachs with equal volume NS. Hypodermically inject 0.4% carrageenin 0.1 mL/10 g to duplicate thrombus model on back parts of mice in each dosage group at 4th continuous treating day, treat continuously till 48 h after model is formed, measure the total length of mice tails and length of black tail, calculate black tail length %. On basis of black tail % in model group, calculate inhibition % of black tail length % of each treating group (thrombosis inhibition %), compare the anti-thrombus effects of different sea cucumber powders. Results see Table 6 below:

TABLE 6

Influences to tail thrombosis caused by carrageenin by treating by irrigating stomachs of mice with different nanometer sea cucumber powders (n = 10, x ± s)

| Group | Black tail length % | Thrombosis inhibition % |
| --- | --- | --- |
| Blank control group | 0*** | — |
| Model group | 67.58 ± 8.66 | — |
| Nanometer cucumaria frondosa powder group | 24.04 ± 14.46*** | 64.43 |
| Nanometer sea stichopus powder group | 14.36 ± 10.98*** | 78.75 |

Note:
***$P < 0.001$ compared with model group

As can be seen from Table 6, compared with model group, black tail lengths % ($p<0.001$) are all significantly reduced by treating by irrigating stomachs of mice with 0.5 g/kg above said two nanometer sea cucumber powders, showing that it has thrombosis inhibition effect for mice tail caused by carrageenin.

CONCLUSION

Different sea cucumber varieties exhibit no significant differences in effect after manufactured into nanometer preparation.

The invention claimed is:

1. A compound sea cucumber product, comprising a sea cucumber powder and a panax pseudo-ginseng saponins extract, wherein the panax pseudo-ginseng saponins extract comprises panax pseudo ginseng saponins R1, Rb1, and Rg1, wherein the sea cucumber powder has an average particle diameter ranging from 100 nm to 200 nm, wherein the sea cucumber powder comprises sea cucumber polysaccharide and a content of sea cucumber polysaccharide ranges from 2.5 wt % to 8.1 wt % and a total content of panax pseudo-ginseng saponins R1, Rb1, and Rg1 ranges from 0.3 wt % to 0.14 wt %, both based on a total weight of the compound sea cucumber product.

2. A dosage form of the compound sea cucumber product of claim 1, in a form of capsule, pill, or granule.

3. The compound sea cucumber product of claim 1, wherein a mass ratio of the sea cucumber powder and the panax pseudo-ginseng saponins extract ranges from 4:1 to 99:1.

4. The compound sea cucumber product of claim 1, wherein the sea cucumber powder is made from a raw material chosen from fresh sea cucumber, dry sea cucumber, semi-dried sea cucumber, and saline sea cucumber of sea stichopus, cucumaria frondosa, or a mixture thereof.

5. The dosage form of claim 2, wherein the dosage form is a capsule containing a mixture of the sea cucumber powder and the panax pseudo-ginseng powder.

6. The dosage form of claim 2, wherein the dosage form is a pill or a granule that comprises the sea cucumber powder, the panax pseudo-ginseng powder, and an excipient, wherein a weight ratio of a sum of the sea cucumber powder and the panax pseudo-ginseng powder to the excipient ranges from 2:1 to 1:1.

7. A method for preparing the compound sea cucumber product of claim 1, the method comprising the steps of:
- (1) Raw material processing: cut a fresh sea cucumber, take out viscus thereof, sufficiently clean them respectively, put them into an airtight container;
- (2) heating a at 70 to 130° C., heat for 1 min to 20 hours;
- (3) Freeze-dry: freeze-dry the gelatinated sea cucumber till the water content is less than 10%;
- (4) Coarse crush: crush the freeze-dried sea cucumber to obtain sea cucumber powder with fineness of 10 to 300 mesh;
- (5) Ultra-micro crush: ultra-micro crush the coarse crushed sea cucumber powder with an airflow crusher, to obtain the ultra-micro sea cucumber powder with fineness of 100 to 3000 mesh;
- (6) Nanometer crush: nanometer crush, by means of a high energy ball grinding mill, the ultra-micro sea cucumber powder obtained by the airflow crusher, till the fineness reaches 10 to 1000 nm, average particle diameter 100 to 200 nm;
- (7) Mix the nanometer sea cucumber powder with panax pseudo-ginseng saponins extract at a ratio of nanometer sea cucumber powder:panax pseudo-ginseng saponins extract equal to 99 to 80 wt %:1 to 20 wt %.

8. The method of claim 7 for preparing the compound sea cucumber product, wherein at step (1), either sea cucumber wall or the sea cucumber wall together with the viscus is ground and put into the airtight container.

9. The method of claim 7 for preparing the compound sea cucumber product, wherein at step (1),
dry sea cucumber, semi-dried sea cucumber, or saline sea cucumber replace the fresh sea cucumber as the raw material, which is, after soaking and cleaning, put into the airtight container.

10. The method of claim 7 for preparing the compound sea cucumber product, wherein the raw material used at step (1) is any one of fresh sea cucumber, dry sea cucumber, semi-dried sea cucumber, and saline sea cucumber from the varieties of sea *stichopus* or *cucumaria frondosa*.

11. The method of claim 7 for preparing the compound sea cucumber product, wherein at step (2) heating and gelatination is performed at 100 to 105° C., 1 hour.

12. The method of claim 7 for preparing the compound sea cucumber product, wherein at step (3) the gelatinated sea cucumber is freeze-dried till the water content is less than 3%.

* * * * *